(12) United States Patent
Minami

(10) Patent No.: US 7,901,352 B2
(45) Date of Patent: Mar. 8, 2011

(54) ENDOSCOPE APPARATUS

(75) Inventor: Itsuji Minami, Saitama (JP)

(73) Assignee: Fujinon Corporation, Saitama (JP)

( * ) Notice: Subject to any disclaimer, the term of this patent is extended or adjusted under 35 U.S.C. 154(b) by 913 days.

(21) Appl. No.: 11/243,969

(22) Filed: Oct. 6, 2005

(65) Prior Publication Data

US 2006/0084841 A1    Apr. 20, 2006

(30) Foreign Application Priority Data

Oct. 8, 2004    (JP) .............................. P2004-295539

(51) Int. Cl.
*A61B 1/04*    (2006.01)
(52) U.S. Cl. ......... 600/168; 600/109; 600/167; 359/380; 359/383; 359/432; 359/694
(58) Field of Classification Search .................. 600/109, 600/118, 130, 160, 167, 168, 174; 359/379, 359/380, 382–384, 421, 422, 432, 677, 694–700
See application file for complete search history.

(56) References Cited

U.S. PATENT DOCUMENTS

| | | | |
|---|---|---|---|
| 5,231,473 A | | 7/1993 | Kawamura et al. |
| 5,302,991 A | * | 4/1994 | Nakayama ...................... 396/81 |
| 5,418,645 A | * | 5/1995 | Coath et al. .................... 359/676 |
| 5,490,015 A | * | 2/1996 | Umeyama et al. ............. 359/824 |
| 5,576,894 A | * | 11/1996 | Kuwana et al. ................ 359/701 |
| 5,661,609 A | * | 8/1997 | Asakura et al. ................ 359/826 |
| 5,691,854 A | * | 11/1997 | Yoshida et al. ................ 359/823 |
| 5,808,813 A | | 9/1998 | Lucey et al. |
| 5,900,995 A | * | 5/1999 | Akada et al. ................... 359/824 |
| 6,134,057 A | * | 10/2000 | Ueyama et al. ................ 359/821 |
| 6,147,814 A | * | 11/2000 | Kitazawa et al. .............. 359/699 |
| 6,392,827 B1 | * | 5/2002 | Ueyama et al. ................ 359/824 |
| 6,425,858 B1 | | 7/2002 | Minami |
| 6,497,652 B2 | | 12/2002 | Akiba |
| 6,661,585 B2 | | 12/2003 | Okawara |
| 6,751,031 B2 | * | 6/2004 | Yasutomi ....................... 359/819 |
| 7,286,754 B2 | * | 10/2007 | Nagae ............................. 396/84 |
| 7,338,219 B2 | * | 3/2008 | Ishizuka et al. ................ 396/349 |
| 7,436,602 B2 | * | 10/2008 | Ishizuka et al. ................ 359/700 |
| 7,447,426 B2 | * | 11/2008 | Okawara ......................... 396/79 |
| 7,463,824 B2 | * | 12/2008 | Yumiki et al. ................... 396/72 |
| 7,488,931 B2 | * | 2/2009 | Wolleschensky et al. ..... 250/234 |
| 7,489,358 B2 | * | 2/2009 | Fujii ............................... 348/335 |
| 7,499,637 B2 | * | 3/2009 | Ishizuka et al. .................. 396/79 |
| 2001/0016680 A1 | * | 8/2001 | Minami et al. ................. 600/167 |

(Continued)

FOREIGN PATENT DOCUMENTS

DE    43 19 502 A1    12/1993

(Continued)

*Primary Examiner* — John P Leubecker
*Assistant Examiner* — Samuel Candler
(74) *Attorney, Agent, or Firm* — Birch, Stewart, Kolasch and Birch, LLP

(57) ABSTRACT

An endoscope apparatus comprises: an insertion section including a distal end; a power changing movable lens that makes observational magnification variable, the power changing movable lens being movably built in an objective optical system provided at the distal end; a linear transmission member that drives the power changing movable lens, the linear transmission member being disposed from a drive section provided at a position other than the insertion section to the distal end; a focus adjusting movable lens that achieves automatic focusing function, the focus adjusting movable lens being movably built in the objective optical system separately from the power changing movable lens; and an actuator that drives the focus adjusting movable lens, the actuator being arranged in the distal end.

8 Claims, 4 Drawing Sheets

U.S. PATENT DOCUMENTS

| | | | |
|---|---|---|---|
| 2001/0044571 A1* | 11/2001 | Mitsumori | 600/167 |
| 2002/0016526 A1* | 2/2002 | Akiba | 600/167 |
| 2002/0026093 A1 | 2/2002 | Ooyatsu | |
| 2002/0075571 A1* | 6/2002 | Chikami et al. | 359/694 |
| 2002/0133059 A1* | 9/2002 | Minami | 600/168 |
| 2003/0072089 A1* | 4/2003 | Yasutomi | 359/701 |
| 2003/0165333 A1* | 9/2003 | Shinohara | 396/72 |

FOREIGN PATENT DOCUMENTS

| | | |
|---|---|---|
| DE | 198 34 207 A1 | 2/1999 |
| EP | 1 088 510 A1 | 4/2001 |
| EP | 1 212 975 A2 | 6/2002 |
| JP | 58-208721 A | 12/1983 |
| JP | 62-187316 A | 8/1987 |
| JP | 6-22903 A | 2/1994 |
| JP | 9-43483 A | 2/1997 |
| JP | 9-253041 A | 9/1997 |
| JP | 2000-147368 A | 5/2000 |
| JP | 2000-271082 A | 10/2000 |
| JP | 2002-48984 A | 2/2002 |
| JP | 2002-153421 A | 5/2002 |
| JP | 02-114006 U | 9/2002 |
| JP | 2002-258166 A | 9/2002 |
| JP | 2002-263058 A | 9/2002 |
| JP | 2003-57528 A | 2/2003 |
| JP | 2003-140030 A | 5/2003 |
| JP | 2003-295049 A | 10/2003 |

* cited by examiner

ENDOSCOPE APPARATUS

BACKGROUND OF THE INVENTION

1. Field of the Invention

The present invention relates to an endoscope apparatus and, in particular, to a structure of an endoscope that performs automatic focus control simultaneously with acquisition of an optically enlarged image of an object to be observed.

2. Description of the Related Art

A electronic endoscope apparatus includes an electronic endoscope (scope) having a CCD (Charge Coupled Device) and the like, which is a solid-state image pickup device, at a distal end thereof, a processor device, and a light source device, and displays an image of an object to be observed on a monitor by picking up an image of an object to be observed by the solid-state image pickup device on the basis of light illumination from the light source device and performing image processing with respect to picture signals by the processor device.

FIG. 6 shows a structure of a distal end of an endoscope with an objective lens moving mechanism in the related art which is applied to electronic endoscopes of this type. In FIG. 6, an observation window 3 is provided at a distal end surface of a supporting section 2 of a distal end 1 of the endoscope, and a CCD 6, which is a solid-state image pickup device, is arranged on the back side of the observation window 3 on an optical path with the intermediary of a prism 4 and a cover glass 5. The picture signals obtained by the CCD 6 are transmitted to the processor device via a signal line 7.

Arranged between the observation window 3 and the prism 4 is a first movable lens 9 and a second movable lens 10 which constitute an objective optical system, and hence a varifocal optical system is established. A holding frame 11 of the first movable lens 9 and a holding frame 12 of the second movable lens 10 are mounted to a cylindrical cam shaft 13 by fitting engaging holes 11A, 12A thereof on an outer periphery of the cam shaft 13. The engaging hole 11A is formed with a cam pin 15, and the engaging hole 12A is formed with a cam pin 16 so as to project therefrom, and the cam shaft 13 is formed with cam grooves 17, 18 at different inclination angles with respect to the axial line thereof. The cam pin 15 is engaged with the cam groove 17 and the cam pin 16 is engaged with the cam groove 18.

A linear transmission member 19 formed of a multicoil spring is connected to the cam shaft, and the other end of the linear transmission member 19 is mounted to a motor or the like provided in an operating unit. Therefore, by rotating the cam shaft 13 via the linear transmission member 19 by driving the motor or the like, the first movable lens 9 and the second movable lens 10 move in the fore-and-aft direction in the direction of the optical axis by engagement between the cam grooves 17, 18 and the cam pins 15, 16, whereby optical change in magnification power (enlargement) or the like is achieved.

On the other hand, as regards the endoscope, there exist a type in which focusing is achieved by driving a focusing lens by a rapid deformation piezoelectric actuator by operating an operating switch of an operating unit as disclosed in JP-A-6-22903.

Alternatively, as shown in JP-A-2002-263058, an endoscope having an automatic focusing mechanism is also manufactured. This automatic focusing mechanism is adapted to drive a movable lens for automatic focusing on the basis of focus estimating signals (high-frequency signals) extracted from the picture signals (predetermined distance measurement area). With the control of the automatic focusing mechanism, the automatically focused object to be observed can be observed on a monitor.

In the case of the endoscope apparatus in which the magnification power is changed optically as described in conjunction with FIG. 6, the magnification power is changed optically (observational distance, observational depth, and focal distance or the like are variable) by moving the second movable lens 10 in association with the movement of the first movable lens 9. In association with the change of the focal point, positional adjustment such as to reduce the distance between the object to be observed and the distal end of the electronic endoscope (scope) and correction of the focus are necessary. However, in an enlarged position, focusability is limited due to the observational depth. Therefore, if further detailed focusing can be performed automatically, an enlarged and clear image of the object to be observed can easily be acquired. In other words, in the related art, when being out of focus, it is necessary to perform focus adjustment operation by minutely moving the distal end of the endoscope for changing the distance with respect to the object to be observed, and such an operation is quite complicated.

On the other hand, since the diameter of the distal end of the endoscope is aimed to be small, an efficient structure and arrangement must be employed in order to provide an automatic focusing mechanism for performing focusing operation automatically in addition to the optical magnification power change mechanism.

SUMMARY OF THE INVENTION

In view of such problems, it is an object of the present invention to provide an endoscope apparatus in which a focused enlarged image can be acquired automatically and easily by arranging an automatic focusing mechanism efficiently in a distal end of a small diameter independently from an optical magnification power change mechanism.

In order to achieve the above-described object, the invention according to a first aspect of the invention is an endoscope apparatus comprising: an insertion section including a distal end; a power changing movable lens that makes observational magnification variable, the power changing movable lens being movably built in an objective optical system provided at the distal end; a linear transmission member that drives the power changing movable lens, the linear transmission member being disposed from a drive section provided at a position other than the insertion section to the distal end; a focus adjusting movable lens that achieves automatic focusing function, the focus adjusting movable lens being movably built in the objective optical system separately from the power changing movable lens; and an actuator (which is compact and is capable of high-velocity driving) that drives the focus adjusting movable lens, the actuator being arranged in the distal end.

The invention according to a second aspect of the invention further comprises an automatic focus control circuit that sets the focus adjusting movable lens to an initial position by the actuator when starting a focusing operation with the automatic focusing function, and controls a movement of the focus adjusting movable lens from the initial position to a focused position.

According to the structure in the first aspect of the invention, with the provision of the focus adjusting movable lens for driving with the rapid actuator separately from the power changing movable lens, fine focusing can be achieved automatically.

According to the structure in the second aspect of the invention, since the focus adjusting movable lens is set to the initial position at the time of focusing operation and the lens movement (position) is controlled from the initial position by controlling the drive pulse of the actuator or by measuring the drive time of the same, automatic focusing control is enabled without providing a specific position detection sensor.

According to the endoscope apparatus of the present invention, while the power changing movable lens is driven by the linear transmission member, the focus adjusting movable lens is driven by the compact actuator arranged in the distal end. Therefore, the automatic focusing mechanism, which is independent from the optical magnification power change mechanism, is arranged efficiently in the distal end of reduced diameter, and a focused enlarged image can be acquired automatically and easily.

According to the structure in the second aspect of the invention, since the automatic focusing control is performed without using the position detection sensor or the like, reduction of the diameter of the endoscope is advantageously achieved.

DETAILED DESCRIPTION OF THE INVENTION

Figure 1:
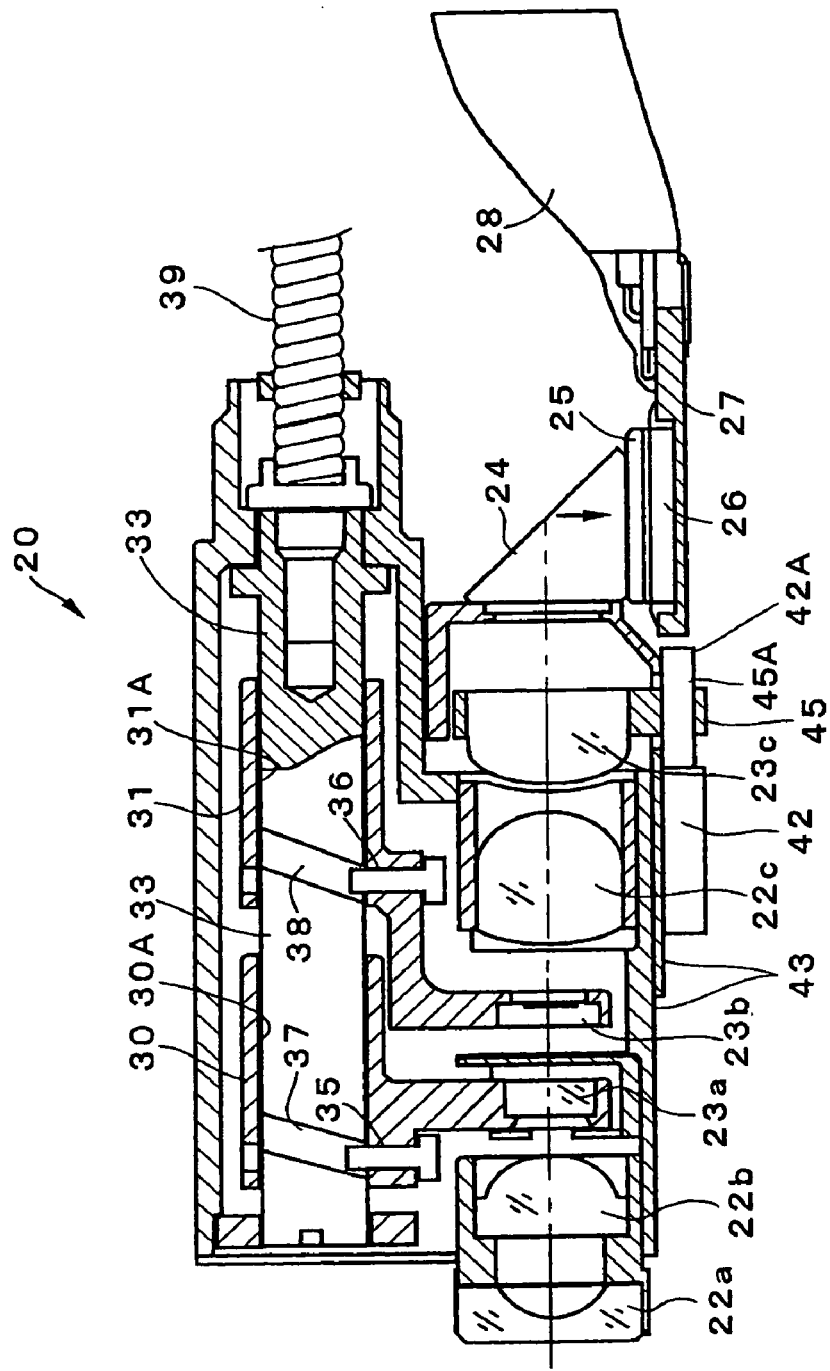
FIG. 1 shows the structure of a distal end of an endoscope with a portion other than a prism and an image pickup device in cross-section taken along the line I-I in FIG. 2.
Figure 4:
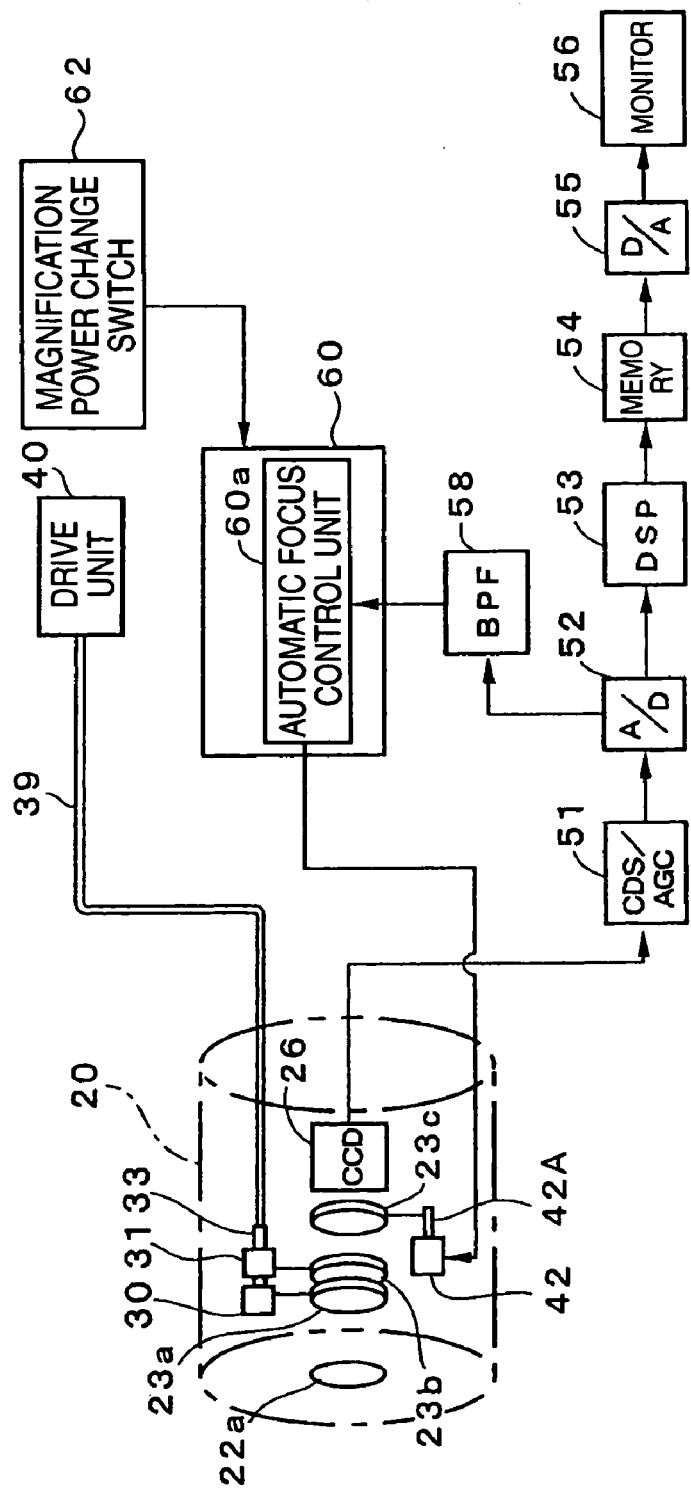
FIG. 4 is a drawing showing a general structure of an electronic endoscope device according to the embodiment.

A structure of an electronic endoscope apparatus according to an embodiment is shown in FIG. 1 and FIG. 4. FIG. 1 shows the structure of a distal end of an endoscope with a portion other than a prism and an image pickup device in cross-section taken along the line I-I in FIG. 2. In FIG. 1, an observation window (lens) 22a, a fixed lens 22b, a first movable lens 23a and a second movable lens 23b for changing the magnification power that are each configured as a varifocal lens, a fixed lens 22c and a third movable lens 23c for focusing are arranged in sequence from the front as an objective optical system at a distal end 20 of the electronic endoscope (scope). A CCD 26 which is a solid state image pickup device is arranged on the backside of the third movable lens 23c with the intermediary of a prism 24 and a cover glass 25. Signals picked up by the CCD 26 are supplied to a processor device via a circuit board 27 and a signal line 28.

The first movable lens 23a is held by a holding frame 30 having an engaging hole 30A, and the second movable lens 23b is held by a holding frame 31 having an engaging hole 31A, and the respective lenses 23a, 23b are attached to a cylindrical cam shaft 33 in a state in which the engaging holes 30A, 31A are fitted on the outer periphery of the cam shaft 33. The engaging hole 30A is formed with a cam pin 35, and the engaging hole 31A is formed with a cam pin 36 so as to project therefrom, and the cam shaft 33 is formed with cam grooves 37, 38 at different inclination angles with respect to the axial line thereof. The cam pin 35 is engaged with the cam groove 37, and the cam pin 36 is engaged with the cam groove 38.

A linear transmission member 39 formed of a multicoil spring or the like is connected to the cam shaft 33, and the other end of the linear transmission member 39 is mounted to a motor shaft of a drive unit 40 (FIG. 4) provided in a operating unit. Therefore, by rotating the cam shaft 33 via the linear transmission member 39 by driving the motor, the first movable lens 23a and the second movable lens 23b are moved in the fore-and-aft direction by the amounts different from each other by engagement of the cam grooves 37, 38 and the cam pins 35, 36, whereby the optical magnification power change (enlargement) is achieved. In other words, the first and the second movable lenses 23a, 23b constitutes the varifocal optical system, and the power magnification is changed optically (observational distance, observational depth, and focal distance are variable) by relatively moving in the fore-and-aft direction. In association with the change of the focal point due to the movement, positional adjustment such as to reduce the distance between the object to be observed and the distal end of the electronic endoscope is performed and then correction of focus is performed, whereby the magnification power on the monitor screen is changed (enlarged).

Figure 3:
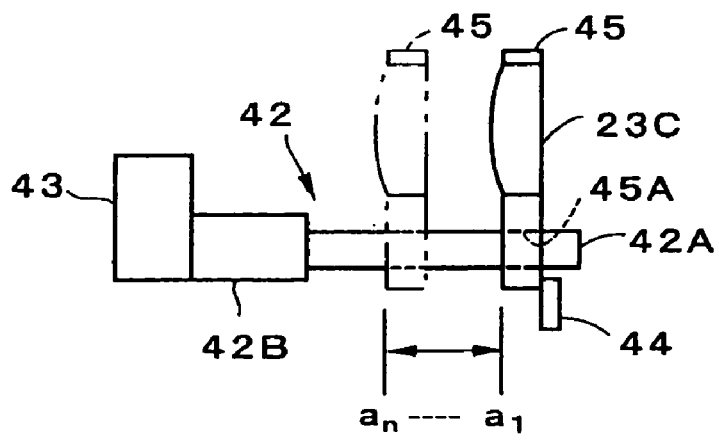
FIG. 3 is a drawing showing a structure and an operational range of a piezoelectric actuator that drives the movable lens for adjusting the focus according to the embodiment.

On the other hand, in order to drive the third movable lens 23c for focusing, a compact and rapid actuator 42 employing a piezoelectric element is mounted to the supporting portion 43, and an engaging hole 45A of a holding frame 45 is movable fitted and arranged on the outer periphery of the drive shaft 42A of the actuator 42. In the actuator 42, as shown in FIG. 3, a piezoelectric element 42B is mounted to the drive shaft 42A, and by moving the drive shaft 42A by the piezoelectric element 42B in the fore-and-aft direction at varying speed, the third movable lens 23c can be moved in the fore-and-aft direction. Other compact linear actuator such as electrostatic actuator may be used as the actuator 42. The present invention will be further illustrated with examples below. Reference numeral 44 in FIG. 3 is a stopper for stopping the third movable lens 23c at an initial position $a_1$.

Figure 2:
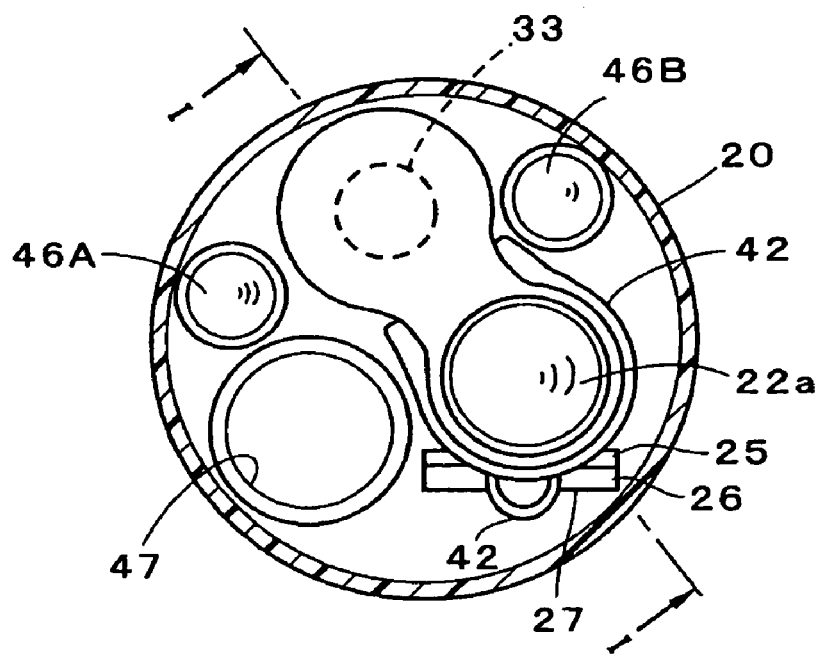
FIG. 2 is a drawing of the distal end of the invention when viewed from the front.

As shown in FIG. 2, in addition to the structure shown in FIG. 1, a light guide, illumination windows 46A, 46B for illuminating light supplied from the light guide, an operative instrument insertion channel 47 and so on are disposed within the distal end 20.

FIG. 4 shows a circuit structure of the electronic endoscope apparatus according to an embodiment, which includes a CDS (relative double sampling)/AGC (automatic gain control) circuit 51 for performing relative double sampling and automatic gain control by inputting the output signal of the above-described CCD 26. On the downstream of the CDS/AGC circuit 51, a A/D converter 52, a DSP (Digital Signal Processor) 53 for performing various image processing, an image memory 54 for storing one frame of image data, D/A converter 55, and a monitor 56 are arranged.

A BPF (Band-Pass Filter) unit 58 that inputs output image signals from the A/D converter 52 and extracts high-frequency components of the picture signals (brightness signals and the like) are provided. In the BPF unit 58, high-frequency components (two types of high-frequency detected signals) for evaluating the focus (or contrast) by two BPF having different pass bands are extracted. In addition, a micro computer 60 for generally managing the control of the electronic endoscope or the processor apparatus is provided, and an auto focus (AF) control unit 60a of passive system is provided in the microcomputer 60. A magnification power change switch 62 for changing the magnification power is provided in the operating unit of the electromagnetic endoscope, and the operating signals are supplied to the microcomputer 60.

The embodiment is configured as described above. In this apparatus, the image of the object to be observed is picked up by the CCD 26 in FIG. 4, and is subjected to the image processing by the circuit from the CDS/AGC circuit 51 to D/A converter 55 on the downstream thereof, whereby the image of the object to be observed is displayed on the screen of the monitor 56. On the other hand, when the magnification power change switch 62 is operated, the linear transmission member 39 is rotated via the drive unit 40, and the cam shaft 33 shown in FIG. 1 is rotated. Accordingly, the first movable lens 23a and the second movable lens 23b are driven and are moved to positions where desired magnification power is provided. In accordance with the change of the position of the focal point due to the movement, the positional adjustment such as to reduce the distance between the object to be observed and the distal end of the electronic endoscope and correction of the focus is performed. Consequently, the optically enlarged image to be observed is picked up by the CCD 26, and an image of the enlarged object to be observed is displayed on the screen of the monitor 56.

In this manner, in the state in which the object to be observed and the distal end of the electronic endoscope are close to each other, the operation for correcting the focus is complicated due to the observational depth, and in a case in which the object to be observed is pulsating, it is specifically difficult to maintain the focused state constantly. Therefore, in the embodiment, the automatic focusing control by the third movable lens 23C for automatic focusing is performed simultaneously with the magnification power changing operation. In other words, in the BPF unit 58 in FIG. 4, the high-frequency components which is a focal point evaluation value is extracted from the image signals, and the movement control of the third movable lens 23c is performed by supplying the high-frequency components to the automatic focus control unit 60a. Then, in this automatic focusing control, the third movable lens 23c is set to an initial position at the beginning, and then movement is started from this initial position.

Figure 5A:
FIGS. 5A and 5B are drawings showing voltage (drive pulse) waveforms for driving the piezoelectric actuator according to the embodiment.
Figure 5B:
Figure 6:
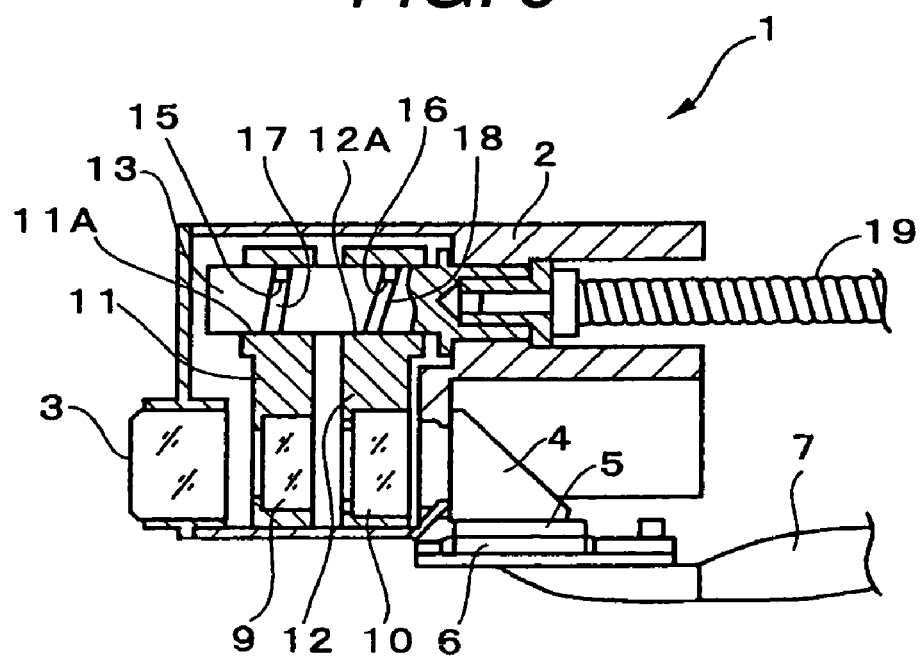
FIG. 6 is a cross-sectional view showing a structure of the distal end of the electronic endoscope in the related art.

In FIG. 5, a voltage waveform to be applied to the piezoelectric element 42B of the actuator 42 is shown. FIG. 5A shows a waveform when the lens 23c is moved backward (assuming that the side of the observation window is the front), FIG. 5B shows a waveform when the lens 23c is moved toward the front. In other words, the lens 23c moves backward at an initial rise where the voltage pulse is slow in FIG. 5A, and moves forward at a fall time where the voltage pulse is slow in FIG. 5B. In the embodiment, for example, the third movable lens 23c is adapted to move one step with one saw-tooth wave in FIGS. 5A and 5B so that the third movable lens 23c can move a range between positions $a_1$ to $a_n$ including n steps (10 steps, for example) as shown in FIG. 3. In the embodiment, by applying 10 or more saw-tooth waves shown in FIG. 5A to the piezoelectric element 42B, the third movable lens 23c is moved to the initial position $a_1$ in FIG. 3 (where it is stopped by a stopper 44) irrespective of the current position of the third movable lens 23c. Accordingly, the initial position $a_1$ of the third movable lens 23c is specified, and hence the position detection sensor is not necessary. The above-described initial position may be $a_n$ at the front end.

Then, by moving the third movable lens 23c in the direction in which the focal point evaluation value increases after having moved from the initial position a1 to the predetermined position, so called climbing action is performed, and then the third movable lens 23c is moved to the focal point by the maximum focal point evaluation value. In this manner, in the embodiment, focusing is achieved by the third movable lens which is separate from the first and second movable lenses 23a, 23b for optically changing the magnification power, finer focusing than in the related art is enabled.

In other words, in the above-described magnification power change function as well, focusing is achieved in a predetermined distance (range) by the first movable lens 23a and the second movable lens 23b. However, depending on the distance between the object to be observed and the distal end of the electronic endoscope, it may go out of focus (in particular, when the scale of enlargement is high). Therefore, the automatic focusing control functions effectively in such a case, and hence the operation and work for moving the distal end of the electronic endoscope to the position where it comes into focus is not any longer necessary.

The entire disclosure of each and every foreign patent application from which the benefit of foreign priority has been claimed in the present application is incorporated herein by reference, as if fully set forth.

What is claimed is:

1. An endoscope apparatus comprising:
  an insertion section including a distal end;
  a power changing movable lens that makes observational magnification variable, the power changing movable lens being movably built in an objective optical system provided in the insertion section at a location adjacent to the distal end;
  an image pickup for converting an image input through the objective optical system into an electrical signal, the image pickup being located closer to an end of the insertion section opposed to the distal end than to the distal end;
  an optical element that receives light from the objective optical system along a viewing direction axis and redirects the received light along an axis perpendicular to the viewing direction axis to reach the image pickup;
  a linear transmission member formed of a multicoil spring that drives a driven portion of the linear transmission member that extends in the viewing direction along a first exterior side portion of the insertion section to move the power changing movable lens in a linear direction of movement, the multicoil spring being disposed from a drive section provided at a position other than the position of the insertion section including the distal end;
  a focus adjusting movable lens that achieves automatic focusing function, the focus adjusting movable lens being movably built in the objective optical system separately from the power changing movable lens; and
  an actuator that drives the focus adjusting movable lens, the actuator being arranged to engage with an outer surface of a supporting portion of the focus adjusting movable lens, the actuator extending in a longitudinal direction along a second exterior side portion of the insertion section that is opposed to the first exterior side portion.

2. The endoscope apparatus according to claim 1, further comprising
  an automatic focus control circuit that sets the focus adjusting movable lens to an initial position by the actuator when starting a focusing operation with the automatic focusing function, and controls a movement of the focus adjusting movable lens from the initial position to a focused position.

3. The endoscope apparatus according to claim 1, wherein the actuator receives a backward saw-tooth waveform that causes the actuator to drive the focus adjusting movable lens backward in a direction away from the distal end at a slow rise time portion of the backward saw-tooth waveform and the actuator receives a forward saw-tooth waveform that causes the actuator to drive the focus adjusting movable lens forward in a direction toward the distal end at a slow fall time portion of the forward saw-tooth waveform.

4. An endoscope apparatus comprising:
   an insertion section including a distal end with a front most portion including an illumination window to supply illuminating light and an observation window that receives the illumination light reflected from an object;
   a power changing movable lens that makes observational magnification variable, the power changing movable lens being movably built in an objective optical system provided in the insertion section at a location adjacent to the distal end of the insertion section so as to be adjacent to the observation window;
   an image pickup for converting an image input through the objective optical system into an electrical signal, the image pickup being located closer to an end of the insertion section opposed to the distal end than to the distal end;
   an optical element that receives light from the objective optical system along a viewing direction axis and redirects the received light along an axis perpendicular to the viewing direction axis to reach the image pickup;
   a linear transmission member that drives the power changing movable lens, the linear transmission member being disposed to extend to the insertion section from a drive section provided at a position other than the insertion section, and the linear transmission member having at least a part thereof extending to the distal end along a first exterior side portion of the insertion section and along an axis parallel to the viewing direction axis and to a linear direction of movement of the power changing movable lens;
   a focus adjusting movable lens that achieves automatic focusing function, the focus adjusting movable lens being movably built in the objective optical system separately from the power changing movable lens; and
   an actuator that drives the focus adjusting movable lens, the actuator being arranged to engage with an outer surface of a supporting portion of the focus adjusting movable lens, the actuator extending along a second exterior side portion of the insertion section that is opposed to the first exterior side portion.

5. The endoscope apparatus according to claim 4, further comprising:
   an automatic focus control circuit that sets the focus adjusting movable lens to an initial position by the actuator when starting a focusing operation with the automatic focusing function, and controls a movement of the focus adjusting movable lens from the initial position to a focused position.

6. The endoscope apparatus according to claim 4, wherein the distal end of the insertion section further includes an operative instrument insertion channel.

7. The endoscope apparatus according to claim 4, wherein the actuator is a piezoelectric or electrostatic linear actuator.

8. The endoscope apparatus according to claim 4, wherein the actuator receives a backward saw-tooth waveform that causes the actuator to drive the focus adjusting movable lens backward in a direction away from the distal end at a slow rise time portion of the backward saw-tooth waveform and the actuator receives a forward saw-tooth waveform that causes the actuator to drive the focus adjusting movable lens forward in a direction toward the distal end at a slow fall time portion of the forward saw-tooth waveform.

* * * * *